US006211247B1

(12) United States Patent
Goodman

(10) Patent No.: US 6,211,247 B1
(45) Date of Patent: Apr. 3, 2001

(54) ADMINISTRATION OF RESVERATROL TO PREVENT OR TREAT RESTENOSIS FOLLOWING CORONARY INTERVENTION

(75) Inventor: David William Goodman, Montreal (CA)

(73) Assignee: Pharmascience Inc, Montreal (CA)

( * ) Notice: Subject to any disclaimer, the term of this patent is extended or adjusted under 35 U.S.C. 154(b) by 0 days.

(21) Appl. No.: 09/434,208

(22) Filed: Nov. 4, 1999

Related U.S. Application Data

(62) Division of application No. 09/078,300, filed on May 13, 1998, now Pat. No. 6,022,901.

(51) Int. Cl.$^7$ .................................................. A01N 31/08
(52) U.S. Cl. .......................................... 514/733; 514/734
(58) Field of Search ..................................... 514/733, 734

(56) References Cited

FOREIGN PATENT DOCUMENTS

| 0773020 A2 | 5/1997 | (EP) . |
| 0773020 A3 | 5/1997 | (EP) . |
| WO99/01148 | 1/1999 | (WO) . |

OTHER PUBLICATIONS

Goldberg et al., "A Global Survey of Trans–Resveratrol Concentrations in Commercial Wines", Am. J. Eno.. Vitic., 46(2):159–165, 1995.*

Bertelli et al. (1995) "Antiplatelet Activity of Synthetic and Natural Resveratrol in Red Wine," *Inst. J. Tiss. Reac. XVII*(1):1–3.

Frankel et al. (1993) "Inhibition of Human LDL Oxidation by Resveratrol," *The Lancet* 341:1104.

Goldberg et al. (1994) "Direct Injection Gas Chromatographic Mass Spectrometric Assay for trans–Resveratrol," *Anal. Chem.* 66:3959–3963.

Goldberg et al. (1995) "A Global Survey of Trans–Resveratrol Concentrations in Commercial Wines," *Am. J. Enol. Vitic.* 46(2):159–165.

Goldberg et al. (1996) "Method to Assay the Concentrations of Phenolic Constituents of Biological Interest in Wines," *Anal. Chem.* 68:1688–1694.

Jang et al. (1997) "Cancer Chemopreventive Activity of Resveratrol, a Natural Product Derived from Grapes," *Science* 275:218–220.

Jeandet et al. (1991) "The Production of Resveratrol (3,5, 4'–trihydroxystilbene) by Grape Berries in Different Development Stages," *Am. J. Enol. Vitic.* 42(1):41–46.

Lee et al. (1994), *Society for Neuroscience Abstracts* 20(1–2):1648.

Moreno–Manas et al. (1985) "Dehydroacetic Acid Chemistry, A New Synthesis of Resveratrole, A Phytoalexine of *Vitis Vinifera*," *Anal. Quim* 81:157–61.

Pace–Asciak et al. (1995) "The Red Wine Phenolics Trans–Resveratrol and Quercetin Block Human Platelet Aggregation and Eicosanoid Synthesis: Implications for Protection Against Coronary Heart Disease," *Clinica Chimica Acta* 235:207–219.

Soleas et al. (1995) "A Derivatized Gas Chromatographic–Mass Spectrometric Method for the Analysis of Both Isomers of Resveratrol in Juice and Wine," *Am. J. Enol. Vitic.* 46(3):346–352.

Tardif et al. (1997) "Probucol and Multivitamins in the Prevention of Restenosis After Coronary Angioplasty," *The New Eng. J. Medicine* 337(6):365–419.

Badimon et al. (1996), "Restenosis Postangioplasty: Role of Local Drug Delivery on its Prevention," *Cardiovascular Risk Factors* 6(6):318–327.

Chen et al. (1996), "Vasorelaxing Activity of Resveratrol and Quercetin in Isolated Rat Aorta," *Gen. Pharmac.* 27(2):363–366.

Feuerstein et al. (1995), "Vascular Restenosis: A Disease in Search of Therapy," *Exp. Opin. Invest. Drugs* 4(3):237–242.

* cited by examiner

*Primary Examiner*—Dwayne C. Jones
(74) *Attorney, Agent, or Firm*—Dianne E. Reed; Reed & Associates

(57) ABSTRACT

A method for preventing or treating restenosis and for preventing the recurrence or progression of coronary heart disease is provided. The method involves administration of a selected active agent to a patient following coronary intervention, e.g., coronary artery bypass surgery, endarterectomy, heart transplantation, heart balloon angioplasty, atherectomy, laser ablation or endovascular stenting. The active agent comprises cis-resveratrol, trans-resveratrol, a mixture thereof, or a pharmacologically acceptable salt, ester, amide, prodrug or analog thereof. Administration may be oral, parenteral, or the like. Pharmaceutical compositions for use in conjunction with the therapeutic method are also provided.

18 Claims, 1 Drawing Sheet

ADMINISTRATION OF RESVERATROL TO PREVENT OR TREAT RESTENOSIS FOLLOWING CORONARY INTERVENTION

TECHNICAL FIELD

This application is a divisional of U.S. patent application Ser. No. 09/078,300, filed on May 13, 1998, which is now U.S. Pat. No. 6,022,901.

This invention relates generally to therapeutic use of resveratrol (3,5,4'-trihydroxy stilbene). More particularly, the invention relates to a method for preventing or treating restenosis following coronary intervention and to a method for preventing the progression or recurrence of coronary artery disease by administering resveratrol to a patient in need of such treatment. The invention additionally relates to pharmaceutical compositions useful in conjunction with the presently disclosed and claimed therapeutic methods.

BACKGROUND

It has been noted that there are a number of biologically active phenolic compounds present in wine, particularly red wine. Such compounds include, for example, catechin, epicatechin, quercetin, rutin, trans-resveratrol, cis-resveratrol, cis-resveratrol glucoside and trans-resveratrol glucoside. See, e.g., Goldberg et al. (1996) *Anal. Chem.* 68:1688–1694. These compounds have been shown to protect low-density lipoproteins against oxidation. The resveratrol isomers, in particular, have been found to promote vascular relaxation through the generation of nitric oxide by the endothelium, and to modulate eicosanoid synthesis in a manner that suggests use in preventing coronary heart disease. Id. at pp. 1688–89). This discovery appears to explain the studies demonstrating that moderate consumption of red wine tends to have a protective effect against heart disease. Bertelli et al. (1995) *Inst. J. Tiss. Reac.* XVII(1):1–3.

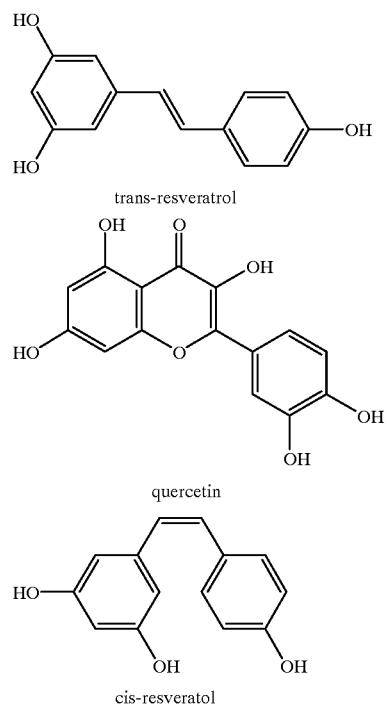

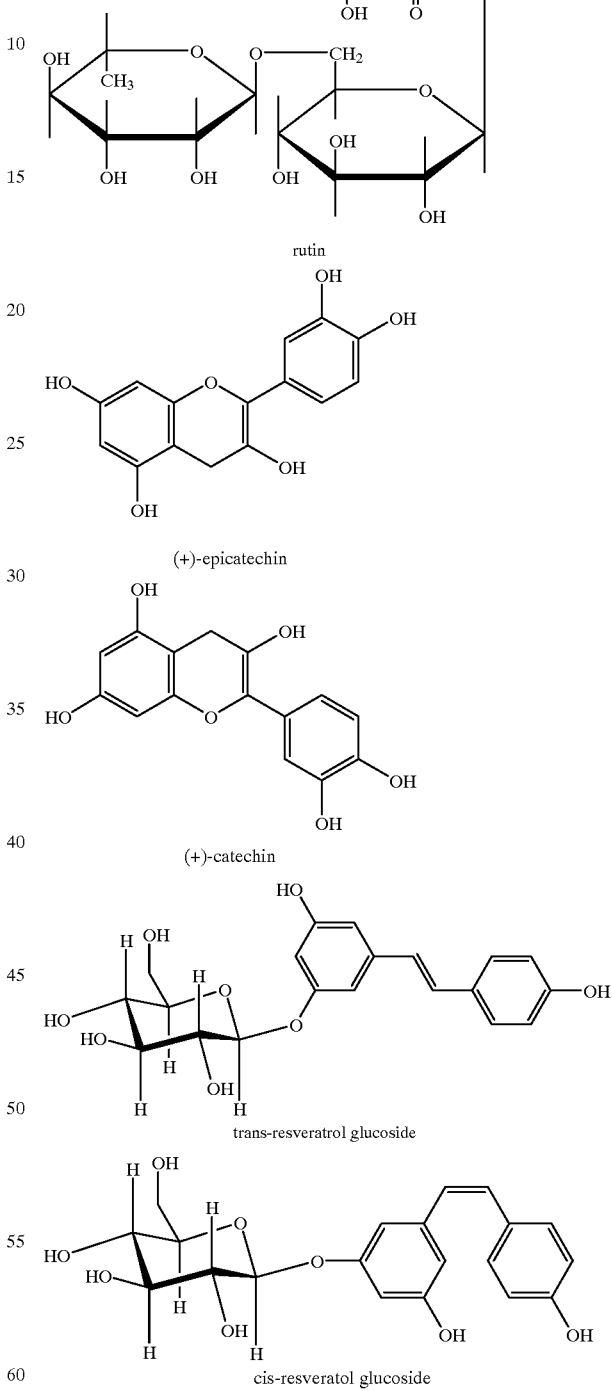

Resveratrol (3,5,4'-trihydroxystilbene) has been identified as a constituent not only of grape skins (Soleas et al. (1995) *Am. J. Enol. Vitic.* 46(3):346–352) but has also been found to be present in ground nuts, eucalyptus, and other plant species. Goldberg et al. (1995), *Am. J. Enol. Vitic.*

46(2):159–165. A great deal of interest has been focused on the compound's antifungal activity and its correlation with resistance to fungal infection. Id. at 159. Resveratrol may be obtained commercially (typically as the trans isomer, e.g. from the Sigma Chemical Company, St. Louis, Mo.), or it may be isolated from wine or grape skins, or it may be chemically synthesized. Synthesis is typically carried out by a Wittig reaction linking two substituted phenols through a styrene double bond, as described by Moreno-Manas et al. (1985) *Anal. Quim* 81:157–61 and subsequently modified by others (Jeandet et al. (1991) *Am. J. Enol. Vitic.* 42:41–46; Goldberg et al. (1994) *Anal. Chem.* 66:3959–63).

There are more studies concerning trans-resveratrol than the cis isomer; however, the cis isomer also appears to be equally important from a biological standpoint. Numerous uses have been proposed and evaluated for the resveratrol isomers. Jang et al. (1997) *Science* 275:218–220, show that resveratrol has cancer chemopreventive activity in assays representing three major stages of carcinogenesis. That is, the authors found that the compound: (1) acted as an antioxidant and antimutagen and induced phase II drug-metabolizing enzymes ("anti-initiation" activity); (2) mediated anti-inflammatory effects and inhibited cyclooxygenase and hydroperoxidase ("antipromotion" activity); and (3) induced human promyelocytic leukemia cell differentiation ("antipromotion" activity). In addition, as noted above, resveratrol has been extensively studied for its correlation to the cardiovascular utility of red wine. See, e.g., Bertelli et al., supra; Pace-Asciak et al. (1995), *Clinica Chimica Acta* 235:207–2191; and Frankel et al. (Apr. 24, 1993), *The Lancet* 341:1104. Neurologic uses have also been proposed (Lee et al. (1994), *Society for Neuroscience Abstracts* 20(1–2): 1648).

The present invention is, however, premised on the discovery that cis- and trans-resveratrol are useful in preventing or treating restenosis and in preventing the progression or recurrence of coronary heart disease. "Restenosis" may be defined as the recurrence of stenosis or artery stricture after corrective surgery, and is viewed as an accelerated form of atherosclerosis. As explained in U.S. Pat. No. 5,616,608 to Kinsella et al., restenosis results from a complex series of fibroproliferative responses to vascular injury, and can occur after coronary artery bypass surgery, endarterectomy and heart transplantation, but is particularly likely to occur after heart balloon angioplasty, atherectomy, laser ablation or endovascular stenting. All of these procedures are generically referred to herein as "coronary intervention." While certain pharmacologically active agents have been proposed for the prevention and treatment of restenosis (e.g., probucol and taxol), there remains a need for a safer, preferably natural active agent which avoids the side effects associated with the currently known and commercially available synthetic agents.

SUMMARY OF THE INVENTION

Accordingly, it is a primary object of the invention to address the above-described need in the art by providing a novel method for preventing or treating restenosis following coronary intervention and for preventing the progression or recurrence of coronary heart disease.

It is another object of the invention to provide such a method by administering a therapeutically effective amount of resveratrol to an individual in need of such treatment.

It is still another object of the invention to provide such a method by administering resveratrol orally.

It is a further object of the invention to provide such a method by administering resveratrol in stereoisomerically pure form, i.e., in either the cis or the trans form.

It is still a further object of the invention to provide a pharmaceutical composition for carrying out the aforementioned therapeutic method.

Additional objects, advantages and novel features of the invention will be set forth in part in the description which follows, and in part will become apparent to those skilled in the art upon examination of the following, or may be learned by practice of the invention.

In one embodiment, then, a method is provided for preventing or treating restenosis in an individual following coronary intervention, comprising treating the individual with a pharmaceutical composition comprising a therapeutically effective amount of an active agent selected from the group consisting of resveratrol and pharmacologically acceptable salts, esters, amides, prodrugs and analogs thereof. Generally, the active agent will be cis-resveratrol, trans-resveratrol, cis-resveratrol glucoside or trans-resveratrol glucoside, and administration will be either oral or parenteral. However, as will be appreciated by those skilled in the art, and as discussed in detail elsewhere herein, other forms of the active agents may also be used, as may a variety of composition types and modes of administration.

In another embodiment, pharmaceutical compositions are provided for carrying out the present therapeutic method. The compositions contain a therapeutically effective amount of an active agent as described above, and pharmacologically acceptable carrier. Preferably, although not necessarily, the compositions are oral dosage forms or liquid formulations suitable for parenteral administration, containing the active agent in unit dosage form.

DETAILED DESCRIPTION OF THE INVENTION

Figure 1:
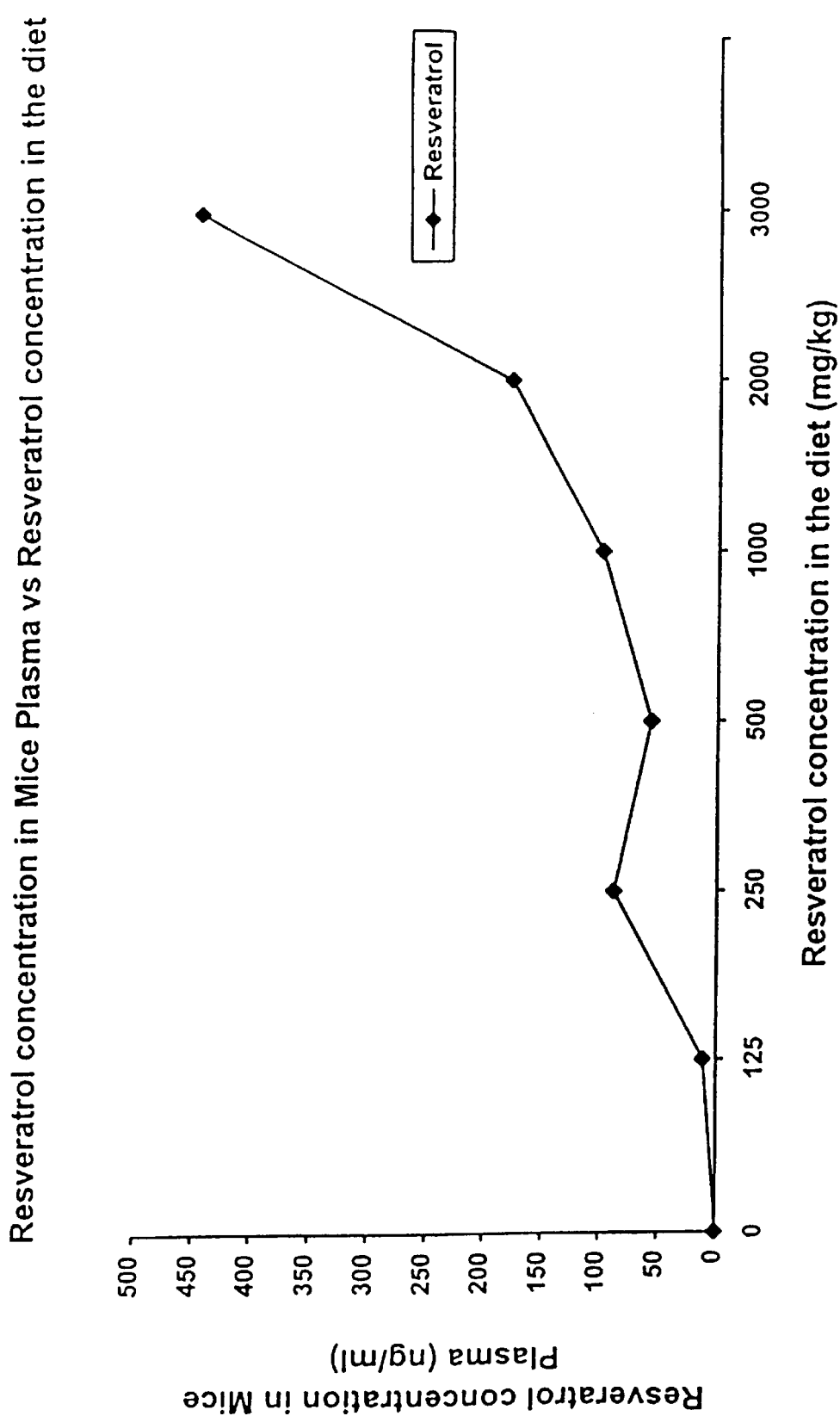
FIG. 1 is a graph illustrating the correlation between the amount of resveratrol fed to mice and the resulting plasma concentration, as evaluated in Example 4.

Overview and Definitions:

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a pharmacologically active agent" includes a combination of two or more pharmacologically active agents, and the like.

In describing and claiming the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect.

The term "resveratrol" is intended to mean either the cis-isomer of resveratrol, the trans-isomer of resveratrol, or a mixture of the two isomers. The term is also intended to include both the naturally occurring active agent and the compound as it may be chemically synthesized in the laboratory.

By "prevention of restenosis" is meant substantially reducing the likelihood that artery stricture will recur following corrective surgery, i.e., coronary artery bypass surgery, endarterectomy or heart transplantation.

"Penetration enhancer" or "permeation enhancer" as used herein relates to an increase in the permeability of the skin or mucosal tissue to the selected pharmacologically active agent, i.e., so that the rate at which the drug permeates through the skin or mucosa is increased.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

By the terms "effective amount" or "therapeutically effective amount" of an agent as provided herein are meant a nontoxic but sufficient amount of the agent to provide the desired therapeutic effect. As will be pointed out below, the exact amount required will vary from subject to subject, depending on the species, age, and general condition of the subject, mode of administration, and the like. Thus, it is not possible to specify an exact "effective amount." However, an appropriate "effective" amount in any individual case may be determined by one of ordinary skill in the art using only routine experimentation.

By "pharmacologically acceptable carrier or excipient" is meant a material which is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmacologically acceptable" salt or a "pharmacologically acceptable" ester of a compound as provided herein is a salt or ester which is not biologically or otherwise undesirable.

Active Agents for Treatment:

The invention, as noted above, involves the administration of resveratrol to an individual in order to prevent restenosis and/or the progression or recurrence of coronary heart disease.

Resveratrol may be administered in natural form, i.e., as isolated from grape skins, wine or other plant-derived compositions, or it may be administered as chemically synthesized in the laboratory (e.g., using the methods of Moreno-Manas et al., Jeandet et al., or Goldberg et al. (1994), cited earlier herein), or as obtained commercially, e.g., from the Sigma Chemical Company (St. Louis, Mo.).

The active agent may be administered in the form of a pharmacologically acceptable salt, ester, amide, prodrug or analog, or as a combination thereof. However, conversion of an inactive ester, amide, prodrug or analog to an active form must occur prior to or upon reaching the target tissue or cell. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (N.Y.: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

Particularly preferred derivatives of cis- and trans-resveratrol are those in which one or more of the compounds' hydroxyl groups, typically the 3-hydroxyl group, is conjugated to a mono- or di-saccharide, generally the 1-position of a monosaccharide. Examples of saccharides which may be conjugated to the resveratrol molecule include, but are not limited to, glucose, galactose, maltose, lactose and sucrose.

Pharmaceutical Formulations and Modes of Administration:

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the active agent in combination with a pharmacologically acceptable carrier and, in addition, may include other pharmaceutical agents, adjuvants, diluents, buffers, etc. The compounds may thus be administered orally, parenterally, transdermally, rectally, nasally, buccally, topically or via an implanted reservoir in dosage formulations containing conventional non-toxic pharmacologically acceptable carriers, adjuvants and vehicles. The preferred mode of administration is oral. The term "parenteral" as used herein is intended to include subcutaneous, intravenous, and intramuscular injection.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see "Remington's Pharmaceutical Sciences", referenced above.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. A more recently revised approach for parenteral administration involves use of a slow release or sustained release system, such that a constant level of dosage is maintained. See, e.g., U.S. Pat. No. 3,710,795.

The compounds of the invention may also be delivered through the skin using conventional transdermal drug delivery systems, i.e., transdermal "patches" wherein the agent is typically contained within a laminated structure that serves as a drug delivery device to be affixed to the skin. In such a structure, the drug composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Alternatively, the pharmaceutical compositions of the invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art.

The pharmaceutical formulation may additionally contain one or more pharmacologically active agents in addition to the compound of interest. These additional active agents will typically be useful for preventing or treating restenosis as well, or they may be useful in countering or inhibiting any side effects, allergies or the like associated with the administration of resveratrol. Preferably, when resveratrol is coadministered with an active agent which is also useful in preventing or treating restenosis, the combination of active agents gives rise to a synergistic effect.

The amount of active compound administered will, of course, be dependent on the subject being treated, the subject's weight, the manner of administration and the judgment of the prescribing physician. In the method of the invention, i.e., preventing or treating restenosis or preventing the progression or recurrence of coronary heart disease, a dosing schedule will generally involve 24-hour intravenous pretreatment with up to about 0.5 to 2.0 mg/kg prior to the coronary intervention, continuous intravenous infusion for 24 hours following the procedure, and then about 0.25 to 2.0 mg/kg continuous intravenous infusion for 24 hours approximately once every three to four weeks.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entirety.

EXAMPLE 1

Trans-resveratrol may be isolated from wine using the procedure of Goldberg et al. (1995) *Am. J Enol. Vitic.* 46(2):159–165, as follows.

Selected wine is maintained at 4° C.'s and tightly stoppered in the dark prior to the isolation procedure. Preferably, isolation of resveratrol from the wine is conducted within two weeks of obtaining the wine. Briefly, a predetermined quantity of wine is passed through a suitable cartridge, e.g., a preconditioned C-18 SP cartridge (Supelco), and the retained trans-resveratrol is eluted with ethyl acetate. The product may be purified using conventional crystallization or chromatographic techniques.

EXAMPLE 2

Laboratory Synthesis of Trans-Resveratrol

Trans-resveratrol is synthesized from appropriately substituted phenols by means of a Wittig reaction modified by Waterhouse from the method of Moreno-Manas and Pleixats, cited supra. The final product is greater than approximately 95% pure as may be confirmed using NMR and UV spectroscopy.

EXAMPLE 3

Conversion of Trans-Resveratrol to Cis-Resveratrol

Trans-resveratrol as isolated from wine, in Example 1, or as chemically synthesized, in Example 2, may be converted to the cis isomer by preparing a solution of the trans isomer in a suitable solvent, e.g., 0.2 M phosphoric acid-acetonitrile (4:1 v/v). The solution is then irradiated for 5–10 min at a wavelength of 254 nm and an intensity of 990 $\mu W/cm^2$. Ultraviolet spectroscopy will confirm that the trans-resveratrol peak, at 306 nm, to be substantially reduced following this procedure. (See Goldberg et al. (1995) *J. Chromatog.* 708:89–98.)

EXAMPLE 4

This experimental work assesses the bioavailability of resveratrol when administered orally to Female Mice Strain A, establishes the relationship between oral administration of resveratrol and the plasma concentration of the female mice, assesses the method of analysis for mouse plasma and establishes the detection limit of resveratrol in animal plasma. The mice were received from the Biological Testing Branch, National Cancer Institute, at 4–6 weeks of age, each having a body weight of approximately 16 g.

After a quarantine period of one week, seven (7) groups each consisting of 10 mice were given resveratrol mixed with Teklad 4% Mouse/Rat chow ad libitum for a 6-week treatment period. As indicated in the table which follows, the concentration of resveratrol ranged from 125 mg/kg of diet to 3000 mg/kg of diet, with one group, as the control group, receiving only the mouse chow.

TABLE 1

| GROUP | Number of Animals | Resveratrol (mg/kg Diet) |
| --- | --- | --- |
| 1 | 10 | Basal Diet |
| 2 | 10 | 125 |
| 3 | 10 | 250 |
| 4 | 10 | 500 |
| 5 | 10 | 1000 |
| 6 | 10 | 2000 |
| 7 | 10 | 3000 |

Parameters monitored during the course of the study included sided-cage observations twice daily and body weight. Blood samples were taken at the end of the treatment period of 6 weeks and kept frozen at −20° C.±5 until the time of analysis. All animals were sacrificed by asphyxiation.

Plasma resveratrol concentration was determined by a liquid—liquid extraction method and reverse phase HPLC at Pharmascience Inc., Bio-analytical Division, Quebec, Canada, as follows. After addition of internal standard and buffer to plasma samples, ethyl acetate was then added. The extracted organic phase was transferred to a clean tube and dried with a nitrogen evaporator. The residue was reconstituted with the mobile phase and then injected to HPLC with UV at 310 nm.

Results:

The results obtained are set forth in the tables which follow, and are also shown in graph form in FIG. 1. It may be concluded that there were no compound-related clinical signs or effects on body weight in any dose groups tested. This study also shows resveratrol is absorbed when it is mixed with mouse chow and given orally to mice, and can be measured in mouse plasma. That is, in FIG. 1, it may be seen that there is a linear relationship between plasma resveratrol levels and the amount of resveratrol administered. Thus, it may be concluded that resveratrol is easily absorbed by the oral route and its detection limit in mouse plasma ranges from 15 to 20 ng/ml.

TABLE 2

Effect of Resveratrol on Body Weight
of Female A/J Mice
INDIVIDUAL BODY WEIGHTS (Grams)
GROUP: 1
DOSE: 0 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 1 | 17.6 | 17.5 | 17.7 | 19.1 | 20.1 | 19.6 | 20.0 | 20.3 | 21.1 | 21.1 | 21.4 | 21.4 |
| 2 | 14.7 | 14.9 | 14.9 | 16.0 | 16.3 | 16.4 | 16.7 | 17.2 | 17.7 | 18.8 | 17.8 | 18.1 |
| 3 | 19.4 | 19.4 | 19.6 | 20.8 | 20.7 | 21.3 | 21.7 | 21.3 | 21.8 | 21.6 | 21.3 | 22.5 |
| 4 | 17.2 | 16.9 | 17.9 | 18.5 | 19.8 | 19.9 | 19.7 | 19.2 | 19.7 | 19.9 | 20.7 | 20.5 |
| 5 | 15.5 | 15.8 | 16.3 | 16.8 | 16.8 | 17.1 | 17.3 | 17.1 | 17.4 | 17.7 | 17.8 | 18.4 |
| 6 | 17.4 | 18.0 | 18.5 | 18.8 | 19.0 | 19.4 | 19.2 | 19.6 | 20.0 | 20.1 | 20.4 | — |
| 7 | 16.8 | 17.2 | 18.0 | 18.8 | 18.4 | 18.5 | 19.2 | 21.1 | 24.1 | 26.0 | — | — |
| 8 | 15.3 | 15.2 | 16.6 | 17.2 | 18.8 | 20.2 | 22.6 | 17.3 | 18.2 | 18.5 | 20.6 | 21.8 |
| 9 | 18.2 | 19.1 | 20.5 | 19.6 | 20.2 | 20.7 | 22.0 | 22.7 | 24.0 | 25.4 | 20.9 | 21.6 |
| 10 | 18.0 | 18.4 | 19.0 | 19.2 | 19.8 | 19.8 | 20.2 | 21.3 | 22.0 | 25.5 | — | — |
| MEAN | 17.0 | 17.2 | 17.9 | 18.5 | 19.0 | 19.3 | 19.9 | 19.7 | 20.6 | 21.6 | 20.1 | 20.6 |
| S.D. | 1.46 | 1.56 | 1.65 | 1.43 | 1.47 | 1.54 | 1.92 | 1.99 | 2.43 | 3.56 | 1.47 | 1.72 |
| N | 10 | 10 | 10 | 10 | 10 | 10 | 10 | 10 | 10 | 10 | 8 | 7 |

—: Data Unavailable

TABLE 3

Effect of Resveratrol on Body Weight
of Female A/J Mice
INDIVIDUAL BODY WEIGHTS (Grams)
GROUP: 2
DOSE: 125 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 11 | 19.2 | 20.0 | 19.6 | 20.7 | 21.9 | 21.5 | 21.6 | 21.3 | 21.6 | 21.7 | 21.6 | 22.2 |
| 12 | 17.0 | 17.4 | 17.8 | 18.2 | 19.0 | 19.1 | 19.7 | 19.4 | 19.9 | 19.9 | 19.7 | 20.0 |
| 13 | 15.4 | 15.9 | 16.2 | 16.6 | 16.9 | 17.2 | 17.4 | 18.2 | 18.5 | 18.4 | 18.3 | 18.7 |
| 14 | 16.7 | 16.9 | 17.4 | 17.3 | 17.7 | 17.6 | 18.0 | 18.5 | 18.9 | 19.1 | 18.9 | 19.6 |
| 15 | 16.2 | 17.6 | 17.4 | 19.1 | 18.8 | 19.2 | 19.2 | 19.2 | 20.4 | 20.7 | 19.8 | 20.2 |
| 16 | 16.5 | 16.4 | 18.1 | 18.6 | 18.8 | 19.6 | 19.5 | 18.8 | 19.8 | 20.2 | 19.9 | 20.0 |
| 17 | 16.8 | 16.6 | 17.8 | 18.8 | 19.2 | 19.6 | 20.5 | 20.9 | 20.2 | 19.8 | 19.8 | 20.4 |
| 18 | 13.4 | 13.1 | 14.1 | 14.8 | 14.4 | 15.0 | 15.1 | 14.8 | 15.2 | 15.3 | 15.2 | 16.0 |
| 19 | 17.0 | 16.8 | 17.8 | 18.3 | 19.2 | 19.6 | 19.7 | 19.9 | 20.1 | 19.5 | 20.3 | 20.6 |
| 20 | 15.8 | 15.5 | 16.8 | 17.2 | 17.8 | 18.5 | 18.7 | 18.8 | 18.9 | 18.6 | 18.4 | 19.4 |
| MEAN | 16.4 | 16.6 | 17.3 | 18.0 | 18.4 | 18.7 | 19.0 | 19.0 | 19.4 | 19.3 | 19.2 | 19.7 |
| S.D. | 1.46 | 1.74 | 1.43 | 1.60 | 1.92 | 1.76 | 1.83 | 1.78 | 1.71 | 1.72 | 1.70 | 1.59 |
| N | 10 | 10 | 10 | 10 | 10 | 10 | 10 | 10 | 10 | 10 | 10 | 10 |

—: Data Unavailable

TABLE 4

Effect of Resveratrol on Body Weight
of Female A/J Mice
INDIVIDUAL BODY WEIGHTS (Grams)
GROUP: 3
DOSE: 250 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 21 | 17.9 | 17.0 | 18.1 | 18.8 | 18.8 | 19.1 | 19.1 | 19.4 | 20.2 | 19.5 | 20.2 | 19.7 |
| 22 | 16.2 | 15.9 | 17.3 | 17.8 | 18.4 | 18.6 | 18.6 | 18.8 | 18.8 | 18.0 | 18.5 | 18.0 |
| 23 | 16.1 | 15.5 | 17.2 | 17.3 | 18.0 | 18.2 | 18.8 | 18.5 | 19.2 | 18.8 | 17.9 | 16.8 |
| 24 | 15.5 | 16.0 | 16.9 | 17.5 | 18.3 | 18.3 | 18.6 | 19.0 | 19.4 | 19.2 | 19.6 | 19.7 |
| 25 | 14.5 | 16.7 | 17.8 | 18.5 | 19.5 | 18.8 | 19.5 | 19.6 | 20.1 | 19.1 | 19.7 | 20.3 |
| 26 | 16.9 | 18.0 | 18.3 | 19.6 | 20.1 | 20.9 | 20.8 | 20.8 | 21.4 | 21.7 | 21.9 | 22.5 |
| 27 | 14.7 | 16.1 | 16.6 | 17.5 | 17.4 | 18.0 | 18.2 | 18.2 | 18.5 | 18.7 | 18.9 | 19.1 |

TABLE 4-continued

Effect of Resveratrol on Body Weight
of Female A/J Mice
INDIVIDUAL BODY WEIGHTS (Grams)
GROUP: 3
DOSE: 250 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 28 | 16.3 | 17.7 | 17.6 | 18.9 | 18.6 | 18.7 | 19.4 | 19.5 | 19.4 | 20.3 | 20.6 | 20.5 |
| 29 | 15.4 | 16.6 | 17.1 | 18.2 | 18.4 | 18.8 | 18.4 | 18.8 | 18.6 | 19.0 | 18.8 | 19.1 |
| 30 | 18.7 | 18.9 | 19.6 | 20.1 | 21.1 | 20.9 | 21.9 | 21.7 | 21.8 | 22.1 | 22.9 | 23.3 |
| MEAN | 16.2 | 16.8 | 17.7 | 18.4 | 18.9 | 19.0 | 19.3 | 19.4 | 19.7 | 19.6 | 19.9 | 19.9 |
| S.D. | 1.33 | 1.07 | 0.87 | 0.94 | 1.09 | 1.04 | 1.17 | 1.08 | 1.13 | 1.33 | 1.56 | 1.93 |
| N | 10 | 10 | 10 | 10 | 10 | 10 | 10 | 10 | 10 | 10 | 10 | 10 |

—: Data Unavailable

TABLE 5

Effect of Resveratrol on Body Weight
of Female A/J Mice
INDIVIDUAL BODY WEIGHTS (Grams)
GROUP: 4
DOSE: 500 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 31 | 16.9 | 17.7 | 17.7 | 18.2 | 18.5 | 18.7 | 19.1 | 19.5 | 20.1 | 20.3 | 19.9 | 20.2 |
| 32 | 15.6 | 16.2 | 16.6 | 17.5 | 18.1 | 18.5 | 18.7 | 19.5 | 19.3 | 19.8 | 19.1 | 19.7 |
| 33 | 16.9 | 18.4 | 18.4 | 18.4 | 18.7 | 19.5 | 20.1 | 20.0 | 20.8 | 20.7 | 20.7 | 20.5 |
| 34 | 16.3 | 17.7 | 17.5 | 17.8 | 18.3 | 18.4 | 19.0 | 19.6 | 19.5 | 19.4 | 18.9 | 19.6 |
| 35 | 17.0 | 17.6 | 17.8 | 18.4 | 18.9 | 18.9 | 19.4 | 20.4 | 20.4 | 20.7 | 20.7 | 20.4 |
| 36 | 18.0 | 18.4 | 19.2 | 19.2 | 19.6 | 20.4 | 20.9 | 21.6 | 20.4 | 20.6 | 20.6 | 20.9 |
| 37 | 18.3 | 19.3 | 18.8 | 19.9 | 20.3 | 21.0 | 20.8 | 21.2 | 20.6 | 21.6 | 21.5 | 21.8 |
| 38 | 15.5 | 17.0 | 17.4 | 18.3 | 18.5 | 19.1 | 18.7 | 19.2 | 19.4 | 19.2 | 19.4 | 19.6 |
| 39 | 17.3 | 18.4 | 18.4 | 18.7 | 19.1 | 19.8 | 20.1 | 20.3 | 20.5 | 21.0 | 21.5 | 21.6 |
| 40 | 13.8 | 14.8 | 15.8 | 16.9 | 16.8 | 17.2 | 16.8 | 17.0 | 17.0 | 17.5 | 17.2 | 17.5 |
| MEAN | 16.6 | 17.5 | 17.8 | 18.3 | 18.7 | 19.2 | 19.4 | 19.8 | 19.8 | 20.1 | 20.0 | 20.2 |
| S.D. | 1.33 | 1.25 | 1.02 | 0.84 | 0.93 | 1.08 | 1.21 | 1.26 | 1.12 | 1.17 | 1.34 | 1.22 |
| N | 10 | 10 | 10 | 10 | 10 | 10 | 10 | 10 | 10 | 10 | 10 | 10 |

—: Data Unavailable

TABLE 6

Effect of Resveratrol on Body Weight
of Female A/J Mice
INDIVIDUAL BODY WEIGHTS (Grams)
GROUP: 5
DOSE: 1000 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 41 | 17.2 | 17.8 | 17.8 | 19.5 | 19.8 | 20.3 | 20.0 | 20.3 | 20.2 | 20.5 | 20.0 | 20.9 |
| 42 | 18.1 | 18.8 | 19.3 | 20.5 | 19.7 | 20.4 | 20.5 | 20.8 | 21.5 | 22.0 | 20.7 | 20.9 |
| 43 | 17.4 | 18.1 | 18.5 | 19.5 | 19.1 | 20.2 | 19.1 | 19.5 | 19.2 | 20.1 | 200 | 20.0 |
| 44 | 17.1 | 18.2 | 18.3 | 19.9 | 18.5 | 20.0 | 19.5 | 21.0 | 21.1 | 21.8 | 21.3 | 20.8 |
| 45 | 15.2 | 16.4 | 16.6 | 17.1 | 17.3 | 18.2 | 18.9 | 18.5 | 18.2 | 18.1 | 18.1 | 18.7 |
| 46 | 14.3 | 15.0 | 15.6 | 16.7 | 17.6 | 18.3 | 18.1 | 18.4 | 18.0 | 18.2 | 18.8 | 18.8 |
| 47 | 16.6 | 17.7 | 18.5 | 18.9 | 19.1 | 19.7 | 20.4 | 21.1 | 21.4 | 20.6 | 20.7 | 21.0 |
| 48 | 16.1 | 16.6 | 17.3 | 18.4 | 18.3 | 18.4 | 18.4 | 19.2 | 20.1 | 20.0 | 19.5 | 19.3 |

TABLE 6-continued

Effect of Resveratrol on Body Weight
of Female A/J Mice
INDIVIDUAL BODY WEIGHTS (Grams)
GROUP: 5
DOSE: 1000 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 49 | 12.8 | 13.5 | 13.8 | 13.2 | 13.7 | 14.0 | 15.1 | 15.1 | 15.5 | 16.1 | 14.7 | 15.2 |
| 50 | 16.1 | 16.7 | 17.9 | 18.6 | 17.9 | 18.5 | 19.5 | 19.4 | 19.3 | 20.2 | 20.8 | 20.5 |
| MEAN | 16.1 | 16.9 | 17.4 | 18.2 | 18.1 | 18.8 | 19.0 | 19.3 | 19.5 | 19.8 | 19.5 | 19.6 |
| S.D. | 1.60 | 1.62 | 1.64 | 2.13 | 1.76 | 1.91 | 1.57 | 1.78 | 1.86 | 1.81 | 1.94 | 1.78 |
| N | 10 | 10 | 10 | 10 | 10 | 10 | 10 | 10 | 10 | 10 | 10 | 10 |

—: Data Unavailable

TABLE 7

Effect of Resveratrol on Body Weight
of Female A/J Mice
INDIVIDUAL BODY WEIGHTS (Grams)
GROUP: 6
DOSE: 2000 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 51 | 17.7 | 17.9 | 18.8 | 19.2 | 20.2 | 20.1 | 20.2 | 20.0 | 20.7 | 20.8 | 21.0 | 21.6 |
| 52 | 16.1 | 17.2 | 17.6 | 17.6 | 18.1 | 18.9 | 19.4 | 19.5 | 19.4 | 20.0 | 19.3 | 20.7 |
| 53 | 15.4 | 17.3 | 17.6 | 17.8 | 18.8 | 18.6 | 18.9 | 19.7 | 20.2 | 20.2 | 19.2 | 20.2 |
| 54 | 15.9 | 16.8 | 17.4 | 17.8 | 18.4 | 18.9 | 18.8 | 19.4 | 19.0 | 20.1 | 19.7 | 19.5 |
| 55 | 17.8 | 19.1 | 19.5 | 19.6 | 20.1 | 20.3 | 20.2 | 20.7 | 21.0 | 21.3 | 20.3 | 21.7 |
| 56 | 15.7 | 15.8 | 16.9 | 16.9 | 18.4 | 18.8 | 19.0 | 19.5 | 19.8 | 18.4 | 19.9 | 19.2 |
| 57 | 16.1 | 14.8 | 17.0 | 16.7 | 18.4 | 18.4 | 18.7 | 18.8 | 19.5 | 18.5 | 18.9 | 19.2 |
| 58 | 17.8 | 16.5 | 19.2 | 19.0 | 20.1 | 20.9 | 20.7 | 21.4 | 21.2 | 20.4 | 21.0 | 21.9 |
| 59 | 17.0 | 16.5 | 18.1 | 17.7 | 19.5 | 20.0 | 19.9 | 20.0 | 20.7 | 20.0 | 20.9 | 21.3 |
| 60 | 13.7 | 13.6 | 15.3 | 14.5 | 15.7 | 16.3 | 16.0 | 16.1 | 16.6 | 16.7 | 17.2 | 18.0 |
| MEAN | 16.3 | 16.6 | 17.7 | 17.7 | 18.8 | 19.1 | 19.2 | 19.5 | 19.8 | 19.6 | 19.7 | 20.3 |
| S.D. | 1.30 | 1.55 | 1.24 | 1.47 | 1.35 | 1.30 | 1.31 | 1.40 | 1.35 | 1.37 | 1.18 | 1.32 |
| N | 10 | 10 | 10 | 10 | 10 | 10 | 10 | 10 | 10 | 10 | 10 | 10 |

—: Data Unavailable

TABLE 8

Resveratrol on Body Weight
of Female A/J Mice
INDIVIDUAL BODY WEIGHTS (Grams)
GROUP: 7
DOSE: 300 (ppm)

| ANIMAL # | 5 DAYS | 8 DAYS | 12 DAYS | 15 DAYS | 19 DAYS | 22 DAYS | 26 DAYS | 29 DAYS | 33 DAYS | 36 DAYS | 40 DAYS | 42 DAYS |
|---|---|---|---|---|---|---|---|---|---|---|---|---|
| 61 | 16.0 | 16.8 | 17.6 | 16.9 | 18.8 | 18.5 | 18.6 | 18.8 | 18.7 | 19.4 | 19.3 | 19.1 |
| 62 | 14.9 | 16.4 | 17.5 | 17.2 | 18.2 | 18.6 | 18.5 | 18.3 | 18.8 | 18.6 | 19.1 | 19.5 |
| 63 | 15.2 | 16.1 | 17.4 | 16.7 | 18.5 | 19.0 | 18.6 | 19.0 | 19.0 | 19.7 | 19.7 | 20.1 |
| 64 | 14.2 | 14.9 | 15.7 | 15.0 | 16.6 | 17.4 | 16.9 | 16.7 | 17.0 | 17.3 | 16.8 | 17.3 |
| 65 | 15.9 | 16.9 | 17.6 | 16.7 | 18.3 | 18.6 | 18.8 | 19.0 | 19.6 | 20.0 | 19.5 | 20.0 |
| 66 | 17.5 | 17.9 | 18.1 | 17.4 | 19.3 | 19.3 | 19.7 | 19.1 | 20.2 | 20.7 | 20.3 | 20.7 |
| 67 | 17.4 | 18.0 | 18.0 | 17.8 | 19.7 | 20.6 | 20.3 | 19.5 | 20.9 | 21.9 | 20.7 | 21.6 |
| 68 | 17.6 | 17.9 | 18.6 | 18.2 | 18.8 | 19.0 | 20.3 | 19.6 | 20.9 | 20.4 | 19.9 | 20.4 |
| 69 | 18.5 | 19.4 | 19.5 | 18.6 | 21.1 | 21.5 | 21.3 | 20.6 | 21.6 | 21.6 | 22.2 | 22.8 |
| 70 | 15.9 | 16.4 | 16.1 | 16.6 | 17.7 | 18.7 | 18.4 | 18.4 | 18.5 | 19.3 | 18.5 | 19.1 |
| MEAN | 16.3 | 17.1 | 17.6 | 17.1 | 18.7 | 19.1 | 19.1 | 18.9 | 19.5 | 19.9 | 19.6 | 20.1 |
| S.D. | 1.38 | 1.26 | 1.10 | 1.00 | 1.20 | 1.15 | 1.26 | 1.01 | 1.39 | 1.37 | 1.41 | 1.50 |
| N | 10 | 10 | 10 | 10 | 10 | 10 | 10 | 10 | 10 | 10 | 10 | 10 |

—: Data Unavailable

TABLE 9

RESVERATROL CONCENTRATION IN MOUSE PLASMA

| Groups | Concentration of Resveratrol per kg of diet (mg/kg diet) | Concentration of Resveratrol in Plasma (ng/ml) | n |
|---|---|---|---|
| 1 | 0 | 0 | 4 |
| 2 | 125 | 10.8 | 5 |
| 3 | 250 | 87.9 | 4 |
| 4 | 500 | 56.8 | 5 |
| 5 | 1000 | 99.0 | 5 |
| 6 | 2000 | 177.7 | 5 |
| 7 | 3000 | 446.7 | 5 |

EXAMPLE 5

Biological Evaluation: Use in Preventing Restenosis in High Cholesteric Rabbits The procedure of U.S. Pat. No. 5,595,974 to Tomaru may be used to evaluate the utility of trans-resveratrol in preventing restenosis in high cholestereric rabbits, as follows:

An injectable trans-resveratrol solution is prepared containing the following components: 1.0 mg trans-resveratrol; 3 mg chlorobutanol (preservative); 0.1 mg gelatin hydrolyzate (stabilizer); 9 mg sodium chloride (isotonic agent); and distilled water containing 2% dimethyl sulfoxide ("DMSO") for injection (to 1 mL).

Test Procedure:

Common iliac arteries of high cholesteric rabbits to which a diet containing 2% of cholesterol is loaded for a month are used as a model for restenosis, wherein the model consists of (1) a heparin group with seven male rabbits and (2) trans-resveratrol solution combined with heparin group with seven male rabbits, weighing between 2.5 kg and 3 kg, respectively.

This model has been most often used whereby many observations have been obtained and hence were used as a model of restenosis after percutaneous transluminal angioplasty of arterial sclerosis in the test. More specifically, a catheter sheath is inserted into the femoral artery of the rabbit and then the common iliac artery is injured by advancing a balloon catheter through the catheter sheath to the common iliac artery. After the common iliac artery is injured, the balloon catheter is further advanced to bifurcation of aorta. After 2 mL of saline is locally injected through the sheath while occluding a proximal portion by inflating the balloon catheter, the blood perfusion is restarted. This is referred to as a control side.

Similarly, 2 mL of saline containing heparin (25 U/kg) or a mixed solution of trans-resveratrol and heparin, that is, 2 mL of saline in which trans-resveratrol and heparin are mixed at a weight ratio of 1:100, is locally injected into the injured common iliac artery and, after retaining the state for 3 minutes, the blood perfusion is restarted. This is referred to as the drug administered side.

The observation by angioscope and angioscopic visualization after one hour shows the presence of occlusive thrombus or mural thrombus on the control side of all animals but does not show the presence of occlusive thrombus on the drug administered side.

Post-operatively, the percent luminal obstruction (%) of both the control side and the drug administered side are compared by continuing the load of high cholesterol for one month. That is, effects for preventing stenosis by local administration of trans-resveratrol is evaluated by angioscopic visualization after one month from vascular injury to compare the percent luminal obstruction (%) caused by intima pachymenia.

The control side to which only saline is administered showed higher percent luminal obstruction (%) by angioscopic visualization after one month and the formation of stenosis in common iliac artery by loading high cholesterol. The drug administrated side to which trans-resveratrol was administered showed remarkably reduced percent luminal obstruction (%) as compared with the group to which only heparin was administered (P<0.05).

The percent luminal obstruction (%) is calculated by the following equation:

Percent luminal obstruction:

$$(\%) = 100 \times [((①+②)/2 = ③)/((①+②)/2]$$

①: Inner diameter of blood vessel near stenosis (proximal portion)

②: Inner diameter of blood vessel near stenosis (distal portion)

③: Minimum inner diameter of blood vessel on stenosis.

EXAMPLE 6

Biological Evaluation: Use in Preventing Restenosis in Humans

The procedure of Tardif et al. (1997), *New England J. Med.* 337(6):365–67 may be carried out as follows.

Study Design and Study Population:

The study is a double-blind, placebo-controlled, randomized trial with four study groups. Patients referred for elective coronary angioplasty are evaluated at least 30 days before the scheduled procedure. Preliminary evaluation includes a medical history taking and physical examination, electrocardiography, blood count, and blood chemistry tests including measurements of serum lipids and glucose and liver, kidney, and thyroid function. Patients are eligible if they were scheduled to undergo standard balloon angioplasty on at least one native coronary artery and have at least one target lesion with stenosis of 50 percent or more of the luminal diameter as measured by calipers on the angiogram. Subject are excluded who are unable to participate in the pretreatment evaluation or unable to return for follow-up; those who have had a myocardial infarction within the previous seven days; those who have undergone angioplasty for another lesion in the preceding six months or who are being treated for a restenotic lesion; and patients undergoing angioplasty of a bypass graft or of a bypassed native vessel with a patent graft.

Randomization and Drug Regimen:

Beginning 30 days before the scheduled angioplasty, patients are randomly assigned to receive one of two treatments: trans-resveratrol alone or placebo. 50 mg trans-resveratrol or placebo tablets are administered twice daily. All patients in whom angioplasty is successful and who did not have procedure-related cardiac complications continue to receive the assigned study treatment until follow-up angiography was performed.

Angioplasty Procedure and Angiographic Methods:

All patients receive aspirin (325 mg daily) for the entire study period. Balloon angioplasty is performed according to standard techniques. Control angiography both before and after angioplasty and at follow-up is preceded by the administration of intracoronary nitroglycerin (0.3 mg). The sequence of contrast injections with the exact degree of angulation is recorded for angiography performed before the procedure, immediately after the final balloon inflation, 15 minutes later, and at follow-up. Electrocardiograms are obtained before angioplasty, immediately thereafter, and daily until discharge. Creatine kinase and creatine kinase MB fraction are measured on the evening after the procedure and the following morning.

Patients are excluded from the study if the stenosed coronary-artery segment could not be dilated; if initially successful angioplasty is followed by persistent abrupt closure; if a Q-wave infarction occurs in the territory of the dilated artery; if angioplasty is unsuccessful, necessitating emergency revascularization; or if the results of angioplasty are suboptimal and a stent was implanted.

Follow-up Evaluation:

Patients who undergo successful angioplasty are discharged with one month's supply of the study medication, aspirin, and any other drugs judged necessary. Patients return at one, three, and six months for a new supply of drugs; at this time, pill counts and a clinical evaluation are performed. Patients are assessed for ischemic symptoms and for any symptoms, whether or not they are related to the study medication or the angioplasty procedure. Compliance is further evaluated by measurements of drug levels in serum at each visit. These levels are not made available to investigators during the trial, in order to maintain blinding. Blood-chemistry values assessed at base line are measured again at discharge and at each follow-up visit. The one-month and six-month visits include treadmill exercise tests. Patients are readmitted for follow-up coronary angiography five to seven months after angioplasty. Those in whom arteriography is performed for clinical reasons before the fifth month return for another angiographic examination at five to seven months if there is no definite arteriographic evidence of restenosis in one or more dilated segments.

Assessment of Diet and Dietary Intervention:

Each patient has four complete food-intake evaluations; the modified Burke questionnaire (Baeuerle et al. (1996) Pathol. Biol. (Paris) 44:29–35) is used at baseline and a food journal at other visits, with questions to assess the intake of fruit, vegetables, and dietary supplements. Food composition is determined according to the Canadian Nutrient File. Patients are given specific dietary counseling at each visit. The American Heart Association Step 1 diet is taught to all patients.

Measurement of Drug Levels:

The level of trans-resveratrol in serum is determined by isocratic reverse-phase high-performance liquid chromatography. All samples are frozen at −70° C. and analyzed in duplicate.

Quantitative Coronary Angiography:

The four coronary arteriograms (obtained before the procedure, immediately after the procedure, 15 minutes after the procedure, and at the final follow-up visit) are analyzed together by experienced technicians supervised by a cardiovascular radiologist who is blinded to the patients' treatment assignments, using the Coronary Measurement System (Medis, Nuenen, the Netherlands). Measurements are made in a single projection, showing the most severe stenosis. The projection that shows the arterial segment with good opacification, as nearly perpendicular to the x-ray beam as possible, is selected for analysis. Whenever possible, the same projection is used in all four arteriograms to allow more accurate comparison.

Definitions and End Points:

Restenosis is evaluated in terms of both numbers of patients and numbers of dilated coronary-artery segments. All measurements are made by quantitative angiographic methods. Only patients in whom at least one lesion was successfully dilated are included in the analysis of restenosis. Successful dilation is defined as residual stenosis of less than 50 percent of the luminal diameter (as measured 15 minutes after the procedure), with improvement of at least 15 percent in luminal diameter as compared with the measurement before the procedure. The angiogram obtained 15 minutes after angioplasty is used in the analysis of outcomes in order to exclude the effects of early elastic recoil, at least in part, from the assessment of restenosis.

The primary end point with respect to efficacy is the extent of restenosis, defined as the reduction in the minimal luminal diameter from the angiogram obtained 15 minutes after angioplasty to that obtained at follow-up. In patients who are undergoing angioplasty on more than one lesion, the means of the luminal diameter for all successfully dilated sites 15 minutes after angioplasty and at follow-up are computed. Restenosis is also defined as a dichotomous outcome variable and analyzed in terms of the change in the percentage of stenosis. A patient is defined as having restenosis if at least one dilated segment had stenosis of 50 percent or more of the luminal diameter at follow-up, with an increase of 15 percent or more in the degree of stenosis from that measured on the angiogram obtained 15 minutes after angioplasty. Only successfully dilated segments were considered in the evaluation of the proportion of segments with restenosis. Major secondary clinical end points were death, myocardial infarction, coronary bypass surgery, and repeated angioplasty.

Statistical Analysis:

For the patients who complete the trial without protocol violations (criteria include taking more than 80 percent of the assigned study medications), the primary end point with respect to efficacy—the extent of restenosis—is evaluated with two-way analysis of covariance with control for the luminal diameter 15 minutes after angioplasty and for the distribution of target vessels. In the intention-to-treat analysis, which includes all randomized patients with successful angioplasty, the dichotomous outcome (restenosis or no restenosis) is analyzed similarly by multiple logistic regression. All patients who withdraw early are considered to have restenosis for purposes of the intention-to-treat analysis. Patients who complete the trial with protocol violations are considered to have restenosis or no restenosis depending on the measurements obtained at the final angiography.

The proportion of dilated segments with restenosis is analyzed by the generalized-estimating-equations technique, which takes into account potential interdependence among multiple segments in the same patient. All secondary end points are analyzed in a way similar to that used for the primary efficacy end point. Depending on the outcome, analysis of covariance or multiple logistic regression is used. The proportions of patients reporting adverse effects of treatment are compared width use of chi-square tests. An interim statistical analysis, based on the Pocock constant-boundary approach, is scheduled after the first 200 patients complete follow-up.

As in the Tardif et al. study pertaining to the efficacy of probucol in preventing restenosis, it is expected that the above evaluation procedure will show a significant reduction in restenosis in patients treated with trans-resveratrol relative to those patients given placebo only.

What is claimed is:

1. A pharmaceutical composition for preventing or treating restenosis in an individual following coronary intervention, comprising: a unit dosage of an active agent selected from the group consisting of resveratrol and pharmacologically acceptable salts, esters, amides, and mono- or di-saccharide conjugates thereof; and a pharmacologically acceptable carrier, wherein the unit dosage of active agent is effective to prevent or treat restenosis in an individual following coronary intervention.

2. The pharmaceutical composition of claim 1, comprising a dosage form suitable for oral administration.

3. The pharmaceutical composition of claim 2, wherein the dosage form comprises a unit dosage of the active agent.

4. The pharmaceutical composition of claim 2, wherein the dosage form comprises a tablet, capsule, solution or suspension.

5. The pharmaceutical composition of claim 1, comprising a liquid preparation suitable for parenteral administration.

6. The pharmaceutical composition of claim 5, wherein the liquid preparation comprises a unit dosage of the active agent.

7. The pharmaceutical composition of claim 5, wherein the pharmacologically acceptable carrier is sterile saline.

8. The composition of claim 1, wherein the active agent is cis-resveratrol or a pharmacologically acceptable salt, ester, amide, or mono- or di-saccharide conjugate thereof.

9. The composition of claim 8, wherein the active agent is cis-resveratrol.

10. The composition of claim 8, wherein the active agent is a mono- or di-saccharide conjugate of cis-resveratrol.

11. The composition of claim 10, wherein the active agent is cis-resveratrol glucoside.

12. The composition of claim 1, wherein the active agent is trans-resveratrol or a pharmacologically acceptable salt, ester, amide, or mono- or di-saccharide conjugate thereof.

13. The composition of claim 12, wherein the active agent is trans-resveratrol.

14. The composition of claim 13, wherein the unit dosage is approximately 50 mg.

15. The composition of claim 12, wherein the active agent is a mono- or di-saccharide conjugate of trans-resveratrol.

16. The composition of claim 15, wherein the active agent is trans-resveratrol glucoside.

17. The composition of claim 1, wherein the active agent comprises a mixture of cis-resveratrol and trans-resveratrol.

18. The composition of claim 1, wherein the unit dosage is approximately 50 mg.

* * * * *